United States Patent [19]
Sattler

[11] Patent Number: 5,747,350
[45] Date of Patent: May 5, 1998

[54] SYSTEM FOR DOSING LIQUIDS

[75] Inventor: Stephan Sattler, Preisenberg, Germany

[73] Assignee: Boehringer Mannheim GmbH, Mannheim, Germany

[21] Appl. No.: 852,572

[22] Filed: May 7, 1997

Related U.S. Application Data

[63] Continuation of Ser. No. 221,010, Apr. 1, 1994, abandoned.

[30] Foreign Application Priority Data

Apr. 2, 1993 [DE] Germany ............... 43 10 808.3

[51] Int. Cl.$^6$ ..................................... G01N 35/10
[52] U.S. Cl. ............... 436/180; 73/864.16; 73/864.87; 422/75; 422/81; 422/100; 436/54
[58] Field of Search ........................ 422/100, 102, 422/81, 75; 436/180, 54; 73/864.13, 864.16, 864.21, 864.81, 864.87

[56] References Cited

U.S. PATENT DOCUMENTS

| | | | |
|---|---|---|---|
| 2,650,256 | 8/1953 | Lingane | 422/75 |
| 3,931,915 | 1/1976 | Downings et al. | 222/327 |
| 4,101,283 | 7/1978 | Sundstrom | 222/333 |
| 4,738,826 | 4/1988 | Harris | 422/102 |
| 4,838,857 | 6/1989 | Strowe et al. | |
| 4,978,335 | 12/1990 | Arthur, III | |
| 5,017,059 | 5/1991 | Davis | 409/131 |
| 5,024,109 | 6/1991 | Romero et al. | |
| 5,047,014 | 9/1991 | Mosebach et al. | 604/67 |
| 5,151,189 | 9/1992 | Ferkany | 422/100 |
| 5,342,298 | 8/1994 | Michaels et al. | 604/65 |

FOREIGN PATENT DOCUMENTS

| | | |
|---|---|---|
| 0 393 354 | 3/1990 | European Pat. Off. . |
| A-26 58 486 B2 | 8/1979 | Germany . |
| A-30 30 879 A1 | 2/1981 | Germany . |
| A-40 20 522 A1 | 1/1992 | Germany . |
| 2-121672 | 5/1990 | Japan . |
| 4-83251 | 7/1992 | Japan . |
| 5-500917 | 2/1993 | Japan . |
| WO 88/10383 | 12/1988 | WIPO . |

OTHER PUBLICATIONS

Fisher Scientific Catalog, p. 1521 (1988).
Compudil Product Information, published by Hook & Tucker Instruments, Ltd.
Kalger Price List, Peter Kalger GmbH, 1984.

*Primary Examiner*—Jan Ludlow
*Attorney, Agent, or Firm*—Nikaido Marmelstein Murray & Oram LLP

[57] ABSTRACT

A system for dosing liquids includes a dosing device, a device for operating the dosing device, a device for entering data and a unit for calculating the dosing displacement. Data are allocated to a dosing device according to the invention which are characteristic for the inside diameter of the dosing device and thus enable precise dosing. In addition the invention concerns a method for dosing using the system according to the invention.

26 Claims, 3 Drawing Sheets

Fig. 1
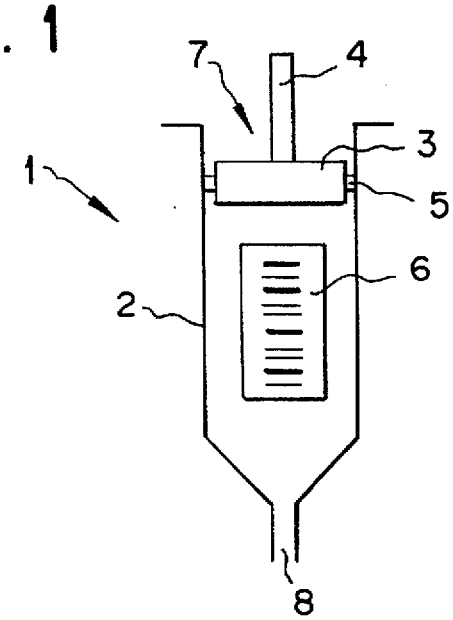
Fig. 2A
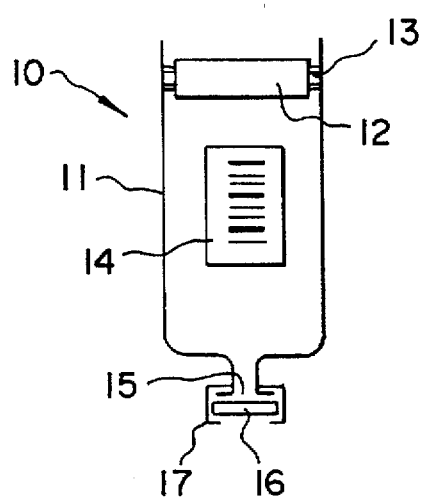
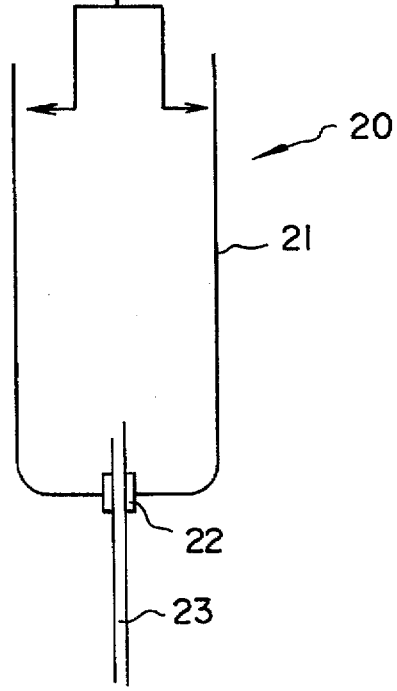
Fig. 2B

SYSTEM FOR DOSING LIQUIDS

This application is a continuation of application Ser. No. 08/221,010, filed Apr. 1, 1994 now abandoned.

The present invention concerns a system for dosing liquids which comprises a dosing device, a device for moving the plunger of the dosing device, a device for entering data and an electronic unit for calculating a dosing displacement. In addition the invention concerns a method for dosing using the aforementioned system and a dosing device used in the system.

Systems which have previously been known for the exact dosing of liquids in analytical instruments have included very expensive dosing devices. Devices which correspond to a plunger sampler are common in the prior art for dosages with low demands on accuracy. The following design is generally known for syringes, it is therefore denoted a syringe body in the following. A cylinder is closed on one side with a wall which has an opening which is small in comparison to the diameter of the cylinder through which liquids can flow out. The small opening can join onto a further cylinder which can be conically tapered on the opposite side to the opening. A plunger forming a seal can move within the cylinder. The liquid which is to be dosed is located in the cavity formed by the plunger and cylinder. Liquid can be pressed out for dosing by movement of the plunger. Such a dosing device is generally denoted a syringe.

A common material for dosing devices of the plunger sampler type are glasses. These materials have the advantage that they are chemically and biologically largely inert so that commonly used liquids in dosing devices can be stored within the dosing device without reactions occurring between liquid and the material of the device. Dosing devices made of glass have the additional advantage that they can be thermally sterilized which is particularly important for their use in clinical analytical systems. Glass dosing devices are produced from long glass tubes. These are then firstly cut up into smaller tubes, one end of which is in turn melted so that a small opening remains. The movable plunger in the cylinder can also be manufactured from glass which, however, is relatively laborious since the plunger has to be ground in such a way that, although it is movable in the cylinder, it nevertheless prevents the efflux of liquid through the space formed between the plunger and cylinder. Therefore materials are preferably used for the plunger which satisfy the requirements for movability and tightness even with the common manufacturing tolerances. Plungers are usually manufactured from rubber or plastics. Dosing devices made of glass usually have a variable inside diameter due to the manufacturing process even in large-scale manufacture. For example the inside diameter even of pre-sorted syringes varies by 0.1 mm at an average inside diameter of about 10 mm. The error which this variation causes in the volume determination can be determined with the error calculation:

$$V = h \cdot \pi \cdot r^2$$
$$dV = h \cdot \pi \cdot 2 \cdot r \cdot dr$$
$$\frac{\Delta V}{V_0} \cdot 100\% = 2 \cdot \frac{\Delta r}{r_0} \cdot 100\%$$

$V$: volume
$h$: dosing displacement
$r$: radius of the cylinder
$\Delta V$: volume error
$\Delta r$: error of the radius Thus the error in the volume determination for the aforementioned data is about 2%. A volume determination with an error of >1% is unacceptable for many dosing purposes especially when they are not the only steps in an analysis.

Dosing devices made of plastic are also known in the prior art. The manufacture of a dosing device made of plastic is sufficiently well-known. If the outer cylinder of the dosing device is made by pressing into a mould then variations in the diameter can be largely avoided. However, the error in the volume dosing cannot be reduced below 0.5% without additional efforts. A disadvantage of dosing devices made of plastic is that, depending on the material, deformations occur to a greater or lesser extent when the device is mechanically stressed such as e.g. in the dosing process itself. Another disadvantage of using dosing devices made of plastic is that contact of the liquid to be dosed with the plastic in many cases leads to undesired reactions. Thus in practice one tries to keep the contact time between liquid and dosing device as short as possible. Systems are known in which liquid is aspirated from a glass vessel by a plastic dosing device in order to be delivered shortly afterwards into a further vessel e.g. an analytical vessel.

So-called precision diluters are common for analyses in which dosing errors have to be reduced to below 0.5%. The way in which this type of dosing device functions is similar to the mechanism of a plunger sampler, but due to the complicated manufacturing process, it is much more expensive than the devices described above. The properties of a precision diluter make it impossible to use this type of dosing device to transport liquids.

Due to the disadvantages of known dosing devices it was the object of the invention to provide a new system which enables precise dosing with a cheaper and simpler device.

The object was achieved by a system for dosing liquids which comprises a dosing device, a device for moving the plunger of the dosing device, a reading instrument to read in data and an electronic unit for calculating a dosing displacement wherein the system possesses data which are characteristic for the inside diameter of the individual dosing device. In addition a method for dosing and a dosing device were found which are suitable for precise dosing.

An essential component of the dosing system according to the invention is a suitable dosing device. Accordingly the invention includes a dosing device which contains a liquid and is characterized in that specific data for its inside diameter are attached to the dosing device. According to the invention the device can correspond to an already described design of the plunger sampler type. Thus the designs denoted plunger sampler and syringe primarily come into consideration. Syringe bodies made of glass are manufactured for example by the "Münnstädter Glaswarenfabrik" Company. Syringe bodies can be ordered directly with details of the desired dimensions. The glasses used can also be selected from a wide range. Preferred glasses are those which are chemically largely inert and thus allow storage of liquids for dosing in the dosing device. The variation in the inside diameter is still about 0.1 mm even in pre-sorted charges.

Syringe bodies made of plastic can for example be obtained from the Treff or Eppendorff Companies. Commercially available dosing devices made of plastic which are also known as dispensers have an accuracy of 0.6% to 1.5%.

Although the variations in the diameter of various syringe bodies is relatively large, observations show that each syringe body has an almost constant inside diameter over its length. If this inside diameter (e.g. in millimeters) corresponding to the individual syringe body is determined and stored in such a way that the data can be related to a particular syringe body, it is then possible to calculate a dosing displacement which enables a precise dosing. The dosing displacement (h) for dosing devices with a preferably cylindrical shape is derived from the volume (V) to be dosed and the individual inside diameter (d) of the dosing device:

$$h = \frac{4 \cdot V}{\pi \cdot d^2}$$

For dosing devices with an arbitrary but constant cross-section this generally gives:

$$h = \frac{V}{A}$$

h: dosing displacement
V: volume to be dosed
A: cross-sectional area of the dosing device.

It is possible to carry out a single dosage with a dosing device, however, it is preferable to use a dosing device for multiple dosing. This can either be achieved by repeatedly drawing liquid into a dosing device according to the invention and dispensing a defined quantity. It is preferable to achieve this by dispensing a defined quantity several times from a filled dosing device without drawing new liquid into the dosing device between the liquid dispensing.

In the case of series of dosing devices it is also possible to divide the inside diameters which occur into groups and to store a characteristic identification or common inside diameter for the respective group of dosing devices instead of one inside diameter.

The determination of the inside diameter of the described devices can be achieved with a number of methods e.g. mechanically by inside diameter determining device 39, which can utilize a micrometer screw or optically using methods of image processing. In a preferred method the inside diameter is measured by an arrangement known to a person skilled in the art consisting of an air jet and reflecting plate for the air.

The determined inside diameter can be stored in various ways e.g. in a computer, on paper or on a magnetic strip. However, storage in the form of a bar code is preferred. The stored data can also contain other relevant information for the analysis e.g. capacity of the dosing device or in the case of filled dosing devices for example type, amount and concentration of the liquid to be dosed. The allocation of data material to the dosing device is preferably achieved by attaching the data carrier directly to the dosing device e.g. in the form of a bar code which is located on the syringe body. It is, however, also possible that the information is located on the packaging of the dosing device. A further possibility of allocation is that the dosing devices are located in a first assembly, the data are present in a second assembly and there are instructions which describe an unequivocal relationship between elements of the two assemblies. The information, therefore, can be spatially separated from the dosing device.

The invention also includes systems for dosing in which the inside diameter of a dosing device is measured within the system with one of the aforementioned methods. The measurement result can be stored and used for dispensing in the same manner as data on the inside diameter which are read in.

A plunger is located within the syringe body of a dosing device according to the invention which forms a seal against the inside walls of the syringe body. This plunger can for example be manufactured from glass, ceramics or metals, however deformable materials are preferred that on the one hand ensure formation of a seal and on the other hand largely avoid dosing errors due to deformation of the plunger e.g. during the dosing process. Preferred materials are synthetic materials such as polyethylene, polypropylene, rubber, silicon rubber and also Teflon and synthetic plastics.

The dosing devices comprising plunger and syringe body can be mounted in the dosing system either empty or preferably filled with a liquid to dose. If a dosing device is used which is filled outside the system then it is preferably sealed. A syringe can for example be sealed by a cap on the cannula. Syringes made of glass are preferred whose outlet is sealed. The seal can for example be manufactured from a thin metal foil or plastics. A seal in the form of a septum is particularly preferred which is for example clamped onto the outlet of a syringe using aluminium sheets. The septum can include materials such as e.g. synthetic materials and plastics which are known from the prior art as being suitable for septa.

If liquids are present in the dosing device then these are preferably aqueous solutions and particularly preferably reagent solutions for carrying out an analysis. A reagent solution can for example contain enzymes, dyes or colour-forming substances, acids, lyes, buffers and other auxiliary substances. Reagent solutions have the property of reacting in a specific manner with one or several substances to be detected so that a detectable signal is formed.

In the system according to the invention the dosing device is mounted with the aid of a holder on a propelling mechanism. The characteristic data for the inside diameter of the dosing device can for example be automatically read in when the dosing device is inserted, e.g. by a bar code reading device or a magnetic strip reader or they can be entered by the user of the system e.g. via a keyboard. It is advantageous when the data on the type, amount and concentration of the material contained in the dosing device is transferred to the system together with data on the inside diameter. The system also has a mechanism which is driven by a motor which is able to move the plunger of the dosing device. Conventional propelling devices for the plunger of the dosing device are for example sold by the Hamilton Company for precision diluters. The motor of the propelling device is controlled by electronics which calculate the control of the motor from data on the dosing device, data on the contents of the dosing device and data that are entered by the user of the system on the dosage to be carried out. In a preferred embodiment a stepping motor is used since it is possible to achieve an exactly defined number of complete or partial revolutions of the motor shaft in these motors via impulse sequences.

The data for a dosage to be carried out can for example be read in by means of a keyboard, a code-strip reader or a magnetic card reader.

The invention also encompasses a process for dosing liquids by a dosing device comprising the steps reading in the characteristic data for the inside diameter of the individual dosing device reading in specific data for a dosage to be carried out calculation of one or several dosing displacements from the data which have been read in carrying out one or several dosing displacements.

Devices for reading in data and the possible contents of the data have already been described. The calculation of a dosing displacement is based on these data. The calculation also takes into account the characteristic data of the system which for example include the relationship between the rotation of the motor shaft and the resulting movement of the plunger. The dosing displacement can be carried out by means of a stepped motor and a mechanism as already described.

The invention also includes a method for analysis using a system for dosing liquids which comprises the following steps:

reading in physical data of the individual dosing device reading in characteristic data for the inside diameter of the individual dosing device reading in specific data for an analysis to be carried out addition of liquid from a dosing device to a sample and detection of one or several signals evaluation of the analysis by relating the amount of liquid delivered from the dosing device to the detected signals.

The invention in addition includes a method for dosing liquids in which the inside diameter of the dosing device is measured within the system.

If several analyses are carried out with one dosing device then data on the dosing device and its contents can be stored and thus do not need to be read-in again before each analysis.

Exact dosages are particularly important for carrying out analyses. In this case two types of analyses and hence also dosing methods have to be differentiated. In a first type of analysis a defined amount of reagent solution is added from a dosing device to the substance to be analysed in an aqueous solution of substances e.g. body fluids such as blood or urine. This procedure can for example be applied to enzymatic analyses. Reactions take place between the analytical solution and reagent solution which lead to a detectable signal such as e.g. a change in colour. The evaluation of the analysis is carried out on the basis of the detectable signal. The dosing method necessary for carrying out such an analysis corresponds essentially to the dosing method described above.

In a second type of analysis the addition of reagent solution to the analytical solution and the detection of a signal is carried out essentially simultaneously. The dosing device according to the invention can be used to add liquid from the dosing device either in small portions or continuously to the analytical solution. The hydrogen ion concentration or the colour of the solution can for example be detected during this addition. By relating the detectable signal to the amount of liquid dispensed by the dosing device it is possible to evaluate the analysis according to methods which are known in principle in the prior art A special case of the analytical method described above is to use a system according to the invention similarly to a burette. For example the dosing device could add reagent liquid to an analytical solution until a user recognizes a change in colour and stops the addition of reagent liquid. The dosing system can show the user the amount of liquid which has been dispensed, e.g. in millimeters, on a display device which one can use to evaluate the analysis.

An advantage of the invention compared to the prior art is that it is possible even with cheap dosing devices to achieve a precise dosage by the use of individual data for the dosing device. The possibility of using pre-filled dosing devices which can be discarded after use not only avoids problems of carry-over e.g. of analytical solutions but also reduces the handling of liquids by the user to a minimum.

BRIEF DESCRIPTION OF THE DRAWINGS

FIGS. 1 to 5 show the special embodiments of a system according to the invention and its individual elements.

FIG. 1: Dosing device in the embodiment of a syringe.

FIGS. 2A–B: Dosing device in the embodiment of a carpule (2a) and a piercing device (2b)

FIG. 3: System for dosing liquids

FIG. 4: FIG. 4 illustrates a packaging configuration of the present invention.

FIG. 1 shows a dosing device (1) according to the invention. The syringe casing (2) has a cylindrical form with two openings. The larger of the two openings represents the plunger opening (7) through which a plunger (3) can be inserted into the syringe casing (2). Liquid can be dispensed from the dosing device (1) through the smaller opening and it is therefore called the outlet (8). The plunger (3) is manufactured from glass, a O-ring (5) made of rubber is placed around it which ensures that the plunger (3) forms a seal when it moves within the syringe casing (2). The plunger (3) is operated by means of a rod (4). The inside diameter of the syringe casing (2) is affixed to the syringe casing (2) as a bar code (6).

Figure 3:
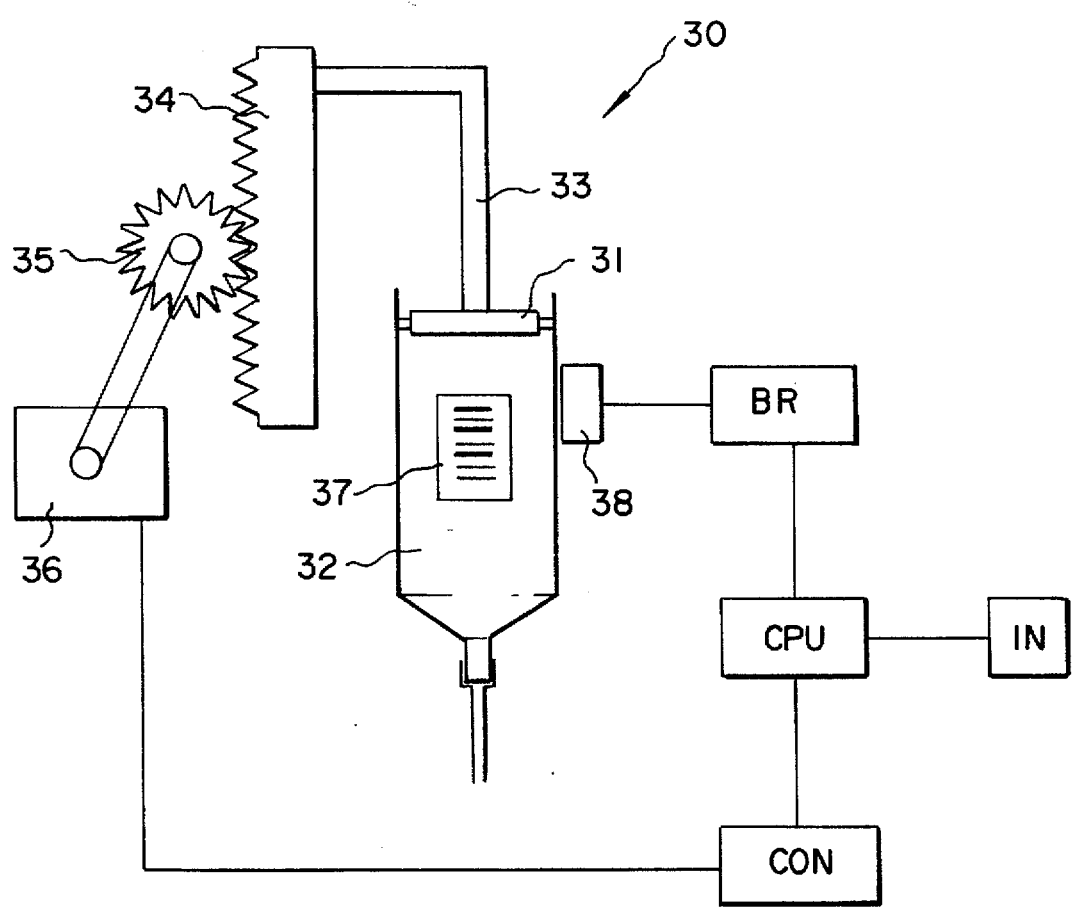

A carpule (10) is shown in FIG. 2A which is also an embodiment of a dosing device according to the invention. The syringe casing (11) is manufactured from glass. A plunger (12) made of silicon plastic is located within this. Sealing is achieved in this case by two lips (13) which are formed by ring-shaped thickenings which encircle the plunger (12) which is in the form of a flat cylinder. A bar code (14) is printed on the syringe casing (11) which comprises a code for the inside diameter of the carpule (10), a description of the liquid in the carpule (10) and its concentration. A septum (16) made of silicon plastic is clamped onto the outlet (15) of the carpule (10) with a thin aluminium sheet (17).

FIG. 2B shows a piercing device (20). It has a cylindrical casing (21) made of glass. One end of this casing (21) is closed by a plug of plastic (22) in which a cannula (23) is inserted both ends of which are bevelled. The carpule (10) can be unsealed with a piercing device (20). For this purpose the carpule (10) is inserted into the piercing device (20) whereby the tip of the cannula (23) extending into the inside of the casing (21) pierces the septum (16). Liquid can now be dispensed from the carpule by movement of the plunger (12).

FIG. 3 shows a diagram of a system (30) for dosing liquids. The plunger (31) of a dosing device (32) is linked mechanically with the lever (33) which can be moved by a gear rack (34). The gear rack (34) is in turn moved by a gear wheel (35) which is driven by a motor (36). When the dosing device (32) is installed in the system (30) the bar code (37) of the dosing device (32) is moved passed a sensor (38). The impulses emitted by the sensor (38) are processed by a bar code reading instrument (BR) and passed onto an electronic unit (CPU) for calculation. The unit (CPU) in addition receives signals from an entry keyboard (IN). In the unit for calculation (CPU), the incoming signals are processed and a dosing displacement is calculated. The unit (CPU) in turn passes signals onto a converter (CON) which controls the motor (36).

Figure 4:
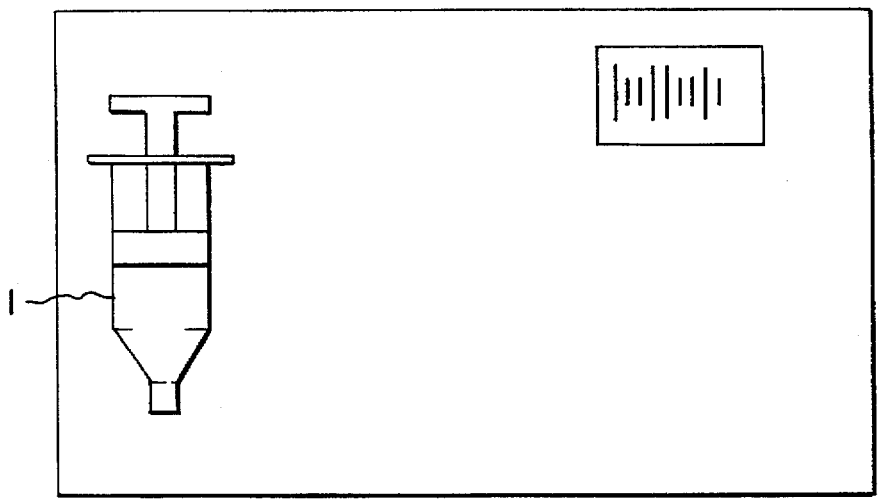

FIG. 4 illustrates a packaging configuration wherein dosing device 1 is provided in a package, with specific inside diameter information being located on the package.

Figure 5A:
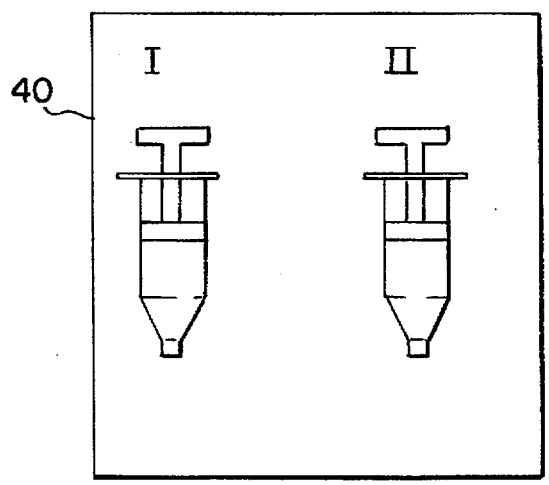
FIGS. 5A–B: a second packaging configuration.
Figure 5B:
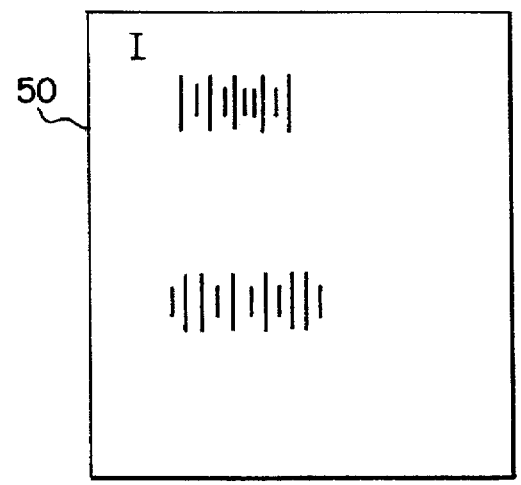

FIGS. 5A–B illustrate a system wherein two dosing devices 1, identified as I and II, are in a first assembly 40, and a second assembly 50 is provided with specific inside diameter information provided thereon in a form which is suitable for conveyance to a reading instrument, and wherein a correlation is provided which describes a critical relationship between the dosing device and the specific inside diameter information.

| List of reference symbols |
| --- |
| (1) dosing device |
| (2) syringe casing |
| (3) plunger |
| (4) rod |
| (5) O-ring |
| (6) bar code |
| (7) plunger opening |
| (8) outlet |
| (9) — |
| (10) carpule |
| (11) syringe casing |
| (12) plunger |
| (13) sealing lip |
| (14) bar code |
| (15) outlet |
| (16) septum |
| (17) aluminium sheet |
| (18) — |
| (19) — |
| (20) piercing device |
| (21) cylindrical casing |
| (22) plastic plug |
| (23) cannula |
| (24) — |
| (25) — |
| (26) — |
| (27) — |
| (28) — |
| (29) — |
| (30) system for dosing liquids |
| (31) plunger |
| (32) dosing device |
| (33) lever |
| (34) gear rack |
| (35) gear wheel |
| (36) motor |
| (37) bar code |
| (38) sensor |

BR: bar code reading instrument
CPU: electronic unit
IN: entry keyboard
CON: converter

I claim:

1. A system for dosing liquids, comprising:

dosing device means for containing a liquid and displacing a predetermined amount of liquid therefrom, said dosing device means having a rigid tube-shape with a specific inner diameter, a plunger moveable along the inner diameter to displace liquid, and information corresponding to the specific inner diameter of the dosing device means provided on the dosing device means, said specific inner diameter being specifically measured for said dosing device means; said system further comprising plunger moving means for moving the plunger a desired distance;

reading means for reading said information; and electronic means coupled to the reading means and the plunger moving means, for receiving the information from the reading means, calculating the desired distance for the plunger to move to displace the predetermined amount of the liquid, and causing the plunger to move the desired distance to displace the predetermined amount of the liquid.

2. System of claim 1, wherein the specific inside diameter information is attached to the dosing device means.

3. System of claim 1, wherein the specific inside diameter information is provided in a form suitable for being conveyed to the reading instrument and spatially separated from the dosing device means.

4. System of claim 1, wherein the specific inside diameter information is stored on a bar code, in the form of a magnetic strip or in a storage chip.

5. System of claim 1, wherein the dosing device means is filled with liquid and sealed.

6. System of claim 5, further including an opening device to open the seal of the dosing device means.

7. System of claim 1, wherein the dosing device means is provided in a package, and the specific inside diameter information is located on the package.

8. System of claim 1, wherein the dosing device means is disposable.

9. System of claim 1, further including an input device coupled to said electronic unit for the manual or automatic input of data for one or more dosages.

10. System of claim 1, further comprising:

a first assembly containing the dosing device means therein; and a second assembly containing the specific inside diameter information thereon in a form which is suitable for being conveyed to the reading instrument, wherein instructions are provided which contain correlation information between the dosing device means and the specific inside diameter information, said instructions being provided on the second assembly.

11. System for dosing liquids as recited in claim 10, wherein said first assembly includes a plurality of dosing device means, and said second assembly includes specific inside diameter information for each of said plurality of dosing device means, wherein the instructions include correlation information which describes the relationship between the plurality of dosing device means and the specific inside diameter information.

12. Process for dosing a liquid, comprising the steps of:

reading in diameter data for a specific inner diameter of an individual dosing device containing the liquid to be dosed, said individual dosing device having a rigid tube-shape with said specific inner diameter being measured for the individual dosing device;

reading in specific dosage data for a dosage to be conducted;

calculating at least one dosing displacement from the diameter and dosage data read in; and conducting the at least one dosing displacement of liquid from the dosing device, thereby displacing a predetermined amount of liquid.

13. Process of claim 12, wherein the liquid is a reagent solution.

14. Process of claim 12, wherein the dosing device is discarded after being emptied.

15. Process of claim 12, wherein the diameter and dosage data for the dosing device and any data relating to the liquid in the dosing device are read once after installation of the dosing device in a dosing system.

16. Method of analysis using a system for dosing liquids, said method comprising the steps of:

reading in diameter data for a specific inner diameter of a dosing device containing the liquid to be dosed, said dosing device having a rigid tube-shape with said specific inner diameter being measured for said dosing device, reading in specific dosage data for a dosage to be conducted;

calculating a dosing displacement from the diameter and dosage data read in; conducting said dosing displacement of liquid from the dosing device to introduce a predetermined amount of liquid into a sample, and detecting at least one signal resulting therefrom; and evaluating the analysis using the amount of liquid displaced from the dosing device and the detected signal.

17. Process of claim 16, wherein the liquid is a reagent solution.

18. Process of claim 16, wherein the dosing device is discarded after being emptied.

19. Process of claim 16, wherein the diameter and dosage data for the dosing device and any data relating to the liquid in the dosing device are read once after installation of the dosing device in the dosing system.

20. A process for dosing liquids with a liquid dosing system, comprising the steps of:

measuring the inside diameter of a dosing device within the system, said dosing device containing the liquid to be dosed;

reading in specific data for the dosage to be conducted;

calculating at least one dosing displacement from the inside diameter measurement and the data which have been read in; and conducting at least one dosing displacement of liquid in accordance with the calculation.

21. Process of claim 20, wherein the liquid is a reagent solution.

22. Process of claim 20, wherein the dosing device is discarded after being emptied.

23. Process of claim 20, wherein the data for the dosage and any data relating to the liquid in the dosing device are read once after installation of the dosing device in the dosing system.

24. System for dosing liquids, comprising:

a dosing device suitable for containing a liquid, having a specific inside diameter and having information corresponding to a desired dosage thereof, said individual dosing device having a plunger to displace liquid;

a plunger moving device operably connected to the plunger and capable of moving the plunger a desired distance;

a reading instrument capable of reading said information; and an electronic unit coupled to said reading instrument and said plunger moving device, said electronic unit for receiving data from the reading instrument, calculating from the desired dosage and specific inside diameter the desired distance for the plunger to move, and causing the plunger to move the desired distance, said system further including a measuring device coupled to said electronic unit, said measuring device measuring the specific inside diameter of the individual dosing device.

25. A system for dosing liquids, said system comprising:

an individual dosing device for containing a liquid, said dosing device having a rigid tube-shape and having a plunger to displace liquid;

a plunger moving device operably connected to the plunger and capable of moving the plunger a desired distance;

a measuring means for measuring a specific inside diameter of the individual dosing device, said measuring means generating data corresponding to the specific inside diameter of the individual dosing device;

an electronic unit coupled to the measuring means and to the plunger moving device, said electronic unit for receiving data from the measuring device and for calculating the desired distance for the plunger to move, said electronic unit also for causing the plunger to move the desired distance, thereby dosing a desired amount of the liquid.

26. A process for dosing liquids with a liquid dosing system, comprising the steps of:

measuring the inside diameter of a dosing device, said dosing device having a rigid tube-shape containing the liquid to be dosed;

reading in specific data for the dosage to be conducted;

calculating at least one dosing displacement from the measurement and the data which have been read in; and conducting at least one dosing displacement of liquid in accordance with the calculation.

* * * * *